United States Patent
Rowe et al.

(10) Patent No.: US 11,611,293 B2
(45) Date of Patent: Mar. 21, 2023

(54) ARTIFICIAL MUSCLES HAVING A RECIPROCATING ELECTRODE STACK

(71) Applicant: Toyota Motor Engineering & Manufacturing North America, Inc., Plano, TX (US)

(72) Inventors: Michael P. Rowe, Pinckney, MI (US); Shardul Panwar, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 588 days.

(21) Appl. No.: 16/818,157

(22) Filed: Mar. 13, 2020

(65) Prior Publication Data
US 2021/0283769 A1    Sep. 16, 2021

(51) Int. Cl.
*H02N 1/00*    (2006.01)
*B25J 9/10*    (2006.01)
*A61F 2/08*    (2006.01)

(52) U.S. Cl.
CPC .................... *H02N 1/002* (2013.01)

(58) Field of Classification Search
CPC ... H02N 1/002; A61F 2/08; A61F 2002/5066; B25J 9/1075
See application file for complete search history.

(56) References Cited

U.S. PATENT DOCUMENTS

| | | | |
|---|---|---|---|
| 5,250,167 A | * | 10/1993 | Adolf ........................ A61F 2/08 204/600 |
| 6,586,859 B2 | | 7/2003 | Kornbluh et al. |
| 7,511,402 B2 | * | 3/2009 | Ito ........................ H02N 11/006 310/800 |

(Continued)

FOREIGN PATENT DOCUMENTS

| CN | 207382213 U | 5/2018 |
|---|---|---|
| CN | 209812321 U | 12/2019 |

(Continued)

OTHER PUBLICATIONS

Li, et al., Fluid-driven origami-inspired artificial muscles (https://www.pnas.org/content/114/50/13132) Published: Nov. 27, 2017.

(Continued)

*Primary Examiner* — Burton S Mullins
(74) *Attorney, Agent, or Firm* — Dinsmore & Shohl LLP

(57) ABSTRACT

An artificial muscle that includes a first end plate opposite a second end plate, a flexible enclosure extending from the first end plate to the second end plate and housing a dielectric fluid, and a reciprocating electrode stack housed within the flexible enclosure and coupled to and extending between the first end plate and the second end plate. The reciprocating electrode stack includes one or more electrode pairs, each electrode pair having a positive electrode and a negative electrode physically coupled to one another along a first edge portion of the positive electrode and the negative electrode. The artificial muscle also includes a plurality of electrode leads electrically coupled to the reciprocating electrode stack. Each individual electrode lead of the plurality of electrode leads extends from an individual electrode of the reciprocating electrode stack to the first end plate or the second end plate.

20 Claims, 7 Drawing Sheets

(56) References Cited

U.S. PATENT DOCUMENTS

| | | | |
|---|---|---|---|
| 7,679,261 | B2 | 3/2010 | Chappaz et al. |
| 7,813,047 | B2 | 10/2010 | Wang et al. |
| 8,237,324 | B2 | 8/2012 | Pei et al. |
| 8,485,581 | B2 | 7/2013 | McKnight et al. |
| 8,779,646 | B2 | 7/2014 | Hino et al. |
| 9,602,641 | B2 | 3/2017 | Kim et al. |
| 10,233,910 | B2 | 3/2019 | Mazzeo et al. |
| 10,995,779 | B2 * | 5/2021 | Keplinger .............. H02N 1/006 |
| 11,060,511 | B1 * | 7/2021 | Kartalov ................... A61F 2/70 |
| 2005/0288597 | A1 | 12/2005 | Kishimoto et al. |
| 2011/0224792 | A1 * | 9/2011 | Groeger ................... A61F 2/08 |
| | | | 623/14.13 |
| 2016/0321880 | A1 | 11/2016 | Hamam et al. |
| 2019/0126516 | A1 | 5/2019 | Pikul et al. |

FOREIGN PATENT DOCUMENTS

| | | | | |
|---|---|---|---|---|
| DE | 102007043481 | A1 * | 3/2009 | ............... A61F 2/08 |
| EP | 0924033 | A2 | 6/1999 | |
| EP | 1221180 | B1 | 7/2002 | |
| GB | 2563896 | B | 7/2019 | |
| JP | 2007097259 | A | 4/2007 | |
| JP | 2007097292 | A | 4/2007 | |
| JP | 2012044447 | A | 3/2012 | |
| JP | 6207478 | B2 | 11/2014 | |
| JP | 6102610 | B2 | 3/2017 | |
| KR | 20070119985 | A | 12/2007 | |
| KR | 20090068130 | A | 6/2009 | |
| KR | 20160117658 | A | 10/2016 | |
| WO | WO-9727822 | A1 * | 8/1997 | ............... A61F 2/08 |
| WO | WO-2007003048 | A1 * | 1/2007 | ............... A61F 2/50 |
| WO | WO-2010037379 | A1 * | 4/2010 | ............... A61F 2/70 |
| WO | 2011054394 | A | 5/2011 | |
| WO | 2015023803 | A1 | 2/2015 | |
| WO | 2018175744 | A1 | 9/2018 | |
| WO | 2018232386 | A1 | 12/2018 | |
| WO | 2019002860 | A1 | 1/2019 | |
| WO | 2019173227 | A1 | 9/2019 | |
| WO | WO-2020180986 | A1 * | 9/2020 | ............. H02N 1/002 |

OTHER PUBLICATIONS

Pikul, et al., Stretchable surfaces with programmable 3D texture morphing for synthetic amouflaging skins (https://science.sciencemag.org/content/358/6360/210). Published: Oct. 13, 2017.

Ceron, et al., Fiber embroidery of self-sensing soft actuators (https://www.mdpi.com/2313-7673/3/24/htm). Published: Sep. 4, 2018.

Cao, et al., Development of a soft untethered robot using artificial muscle actuators (https://www.spiedigitallibrary.org/conference-proceedings-of-spie/10163/101631X/Development-of-a-soft-untethered-robot-using-artificial-muscle-actuators/10.1117/12.2260375.short?SSO=1). Published: Apr. 17, 2017.

Acome, et al., Hydraulically amplified self-healing electrostatic actuators with muscle-like performance, Keplinger Science, Jan. 5, 2018; vol. 359, Issue 6371, pp. 61-65.

Shane Mitchell, et al., "An Easy-To-Implement Toolkit To Create Versatile And High-Performance HASEL Actuators For Untethered Soft Robots," Journal Article, Advanced Science 6(14):1900178, Jun. 2019, URL: https://www.researchgate.net/figure/Generalized-principle-of-zipping-mode-actuation-in-HASEL-actuators-As-voltage-is_fig1_333725822, 15 pages.

* cited by examiner

ARTIFICIAL MUSCLES HAVING A RECIPROCATING ELECTRODE STACK

TECHNICAL FIELD

The present specification generally relates to artificial muscles and, more specifically, to artificial muscles with a reciprocating electrode stack housed in a flexible enclosure.

BACKGROUND

Current robotic technologies rely on rigid components, such as servomotors to perform tasks, often in a structured environment. This rigidity presents limitations in many robotic applications, caused, at least in part, by the weight to power ratio of servomotors and other rigid robotics devices. The field of soft robotics improves on these limitations by using artificial muscles and other soft actuators. Artificial muscles attempt to mimic the versatility, performance, and reliability of biological muscle. Some artificial muscles rely on fluidic actuators, but fluidic actuators require a supply of pressurized gas or liquid and fluid transport must occur through systems of channels and tubes, limiting the speed and efficiency. Other artificial muscles use thermally activated polymer fibers, but these are difficult to control and operate at low efficiencies.

One particular artificial muscle design is described in the paper titled "*Hydraulically amplified self-healing electrostatic actuators with muscle-like performance*" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). These hydraulically amplified self-healing electrostatic (HASEL) actuators use electrostatic and hydraulic forces to achieve a variety of actuation modes. However, HASEL actuator artificial muscles use single pairs of electrodes to cause articulation and stacks of HASEL actuators to achieve a greater stroke and thus the electrode density and actuator power per unit volume of HASEL actuators is limited.

Accordingly, a need exists for improved artificial muscles that have a high electrode density and thus have a high actuation power per unit volume.

SUMMARY

In one embodiment, an artificial muscle includes a first end plate opposite a second end plate, a flexible enclosure extending from the first end plate to the second end plate and housing a dielectric fluid, and a reciprocating electrode stack housed within the flexible enclosure and coupled to and extending between the first end plate and the second end plate. The reciprocating electrode stack includes one or more electrode pairs, each electrode pair having a positive electrode and a negative electrode physically coupled to one another along a first edge portion of the positive electrode and the negative electrode. The artificial muscle also includes a plurality of electrode leads electrically coupled to the reciprocating electrode stack. Each individual electrode lead of the plurality of electrode leads extends from an individual electrode of the reciprocating electrode stack to the first end plate or the second end plate.

In another embodiment, a method of contracting an artificial muscle includes generating voltage using a voltage source electrically coupled to a plurality of electrode leads of an artificial muscle. The artificial muscle further includes a first end plate opposite a second end plate, a flexible enclosure extending from the first end plate to the second end plate and housing a dielectric fluid, and a reciprocating electrode stack housed within the flexible enclosure and coupled to and extending between the first end plate and the second end plate. The reciprocating electrode stack also includes a plurality of electrodes arranged in one or more electrode pairs, each electrode pair having a positive electrode and a negative electrode physically coupled to one another along a first edge portion of the positive electrode and the negative electrode and each individual electrode electrically coupled to an individual electrode lead of the plurality of electrode leads. The method also includes applying voltage generated by the voltage source to the reciprocating electrode stack, thereby inducing contraction of each electrode pair such that the first end plate and the second end plate and drawn toward one another, contracting the artificial muscle into a contracted state.

In yet another embodiment, an artificial muscle includes a first end plate opposite a second end plate, a flexible enclosure extending from the first end plate to the second end plate and housing a dielectric fluid. And a reciprocating electrode stack housed within the flexible enclosure and coupled to and extending between the first end plate and the second end plate. The reciprocating electrode stack includes a plurality of cylindrical electrode pairs. Each cylindrical electrode pair includes a positive electrode and a negative electrode physically coupled to one another along a first edge portion of the positive electrode and the negative electrode. Adjacent cylindrical electrode pairs are physically connected to each other along a second edge portion of one of the two cylindrical electrodes of each adjacent cylindrical electrode pair. In addition, the second edge portion of each cylindrical electrode is diametric the first edge portion. The artificial muscle also includes a plurality of spiral electrode leads electrically coupled to the reciprocating electrode stack. Each individual spiral electrode lead of the plurality of spiral electrode leads extends from an individual cylindrical electrode of the reciprocating electrode stack to the first end plate or the second end plate and curls around the reciprocating electrode stack.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
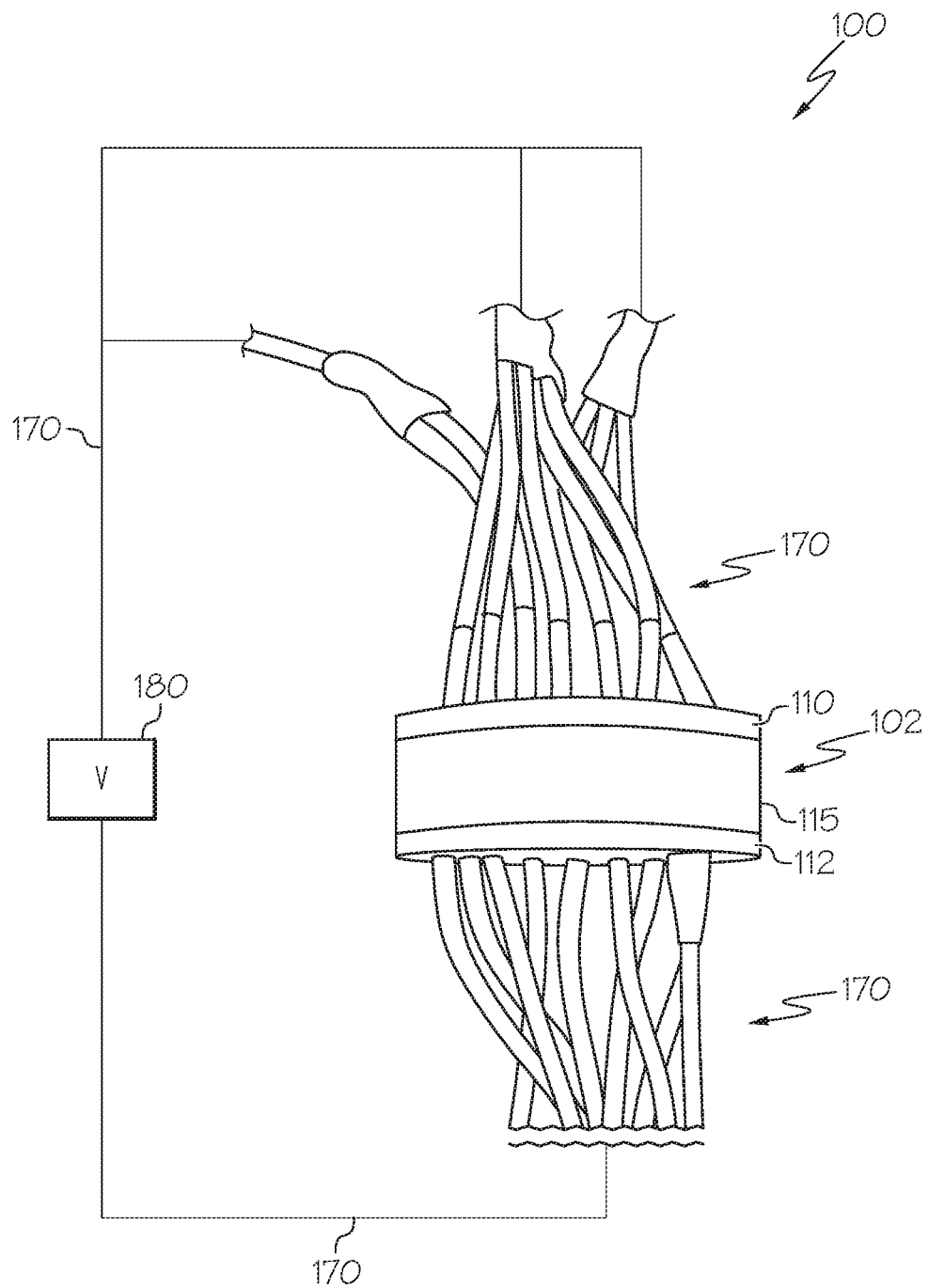
FIG. 1A depicts a side view of an artificial muscle that includes a reciprocating electrode stack housed within a flexible enclosure, where the artificial muscle is in a contracted state, according to one or more embodiments shown and described herein.

Referring generally to the figures, embodiments of the present disclosure are directed to artificial muscles to provide soft actuators for use in a variety of applications, such as robotics. The artificial muscles described herein include a reciprocating electrode stack extending between a pair of end plates and housed in a flexible enclosure with a dielectric fluid. The reciprocating electrode stack includes one or more electrode pairs that each include a positive and a negative electrode physically coupled to one another along one edge. Further, when the reciprocating electrode stack includes multiple electrode pairs, electrodes of adjacent pairs are physically connected along an opposite edge such that the electrodes are connected in an alternating, zigzag pattern.

The arrangement of the reciprocating electrode stack increases the electrode density per volume of the artificial muscle when compared to previous artificial muscles arrangements. For example, the artificial muscle described herein that includes a reciprocating electrode stack has greater than five times the electrode density per volume of HASEL actuator. Increasing the electrode density per volume improves the artificial muscle performance by increasing the actuation force per unit volume. The artificial muscle also includes a plurality of electrode leads that curl around the reciprocating electrode stack to allow the electrode leads to be disposed together with the reciprocating electrode stack and the dielectric fluid in the flexible enclosure without increasing the length of artificial muscle. Embodiments of artificial muscles will now be described and, whenever possible, the same reference numerals will be used throughout the drawings to refer to the same or like parts.

Referring now to FIGS. 1A-2B, an artificial muscle 100 comprising a reciprocating electrode stack 120 extending between a first end plate 110 and a second end plate 112 and housed within a flexible enclosure 115 is schematically depicted. The artificial muscle 100 is electrically coupled to a voltage source 180, for example, using external transmission lines 170. In operation, applying voltage generated by the voltage source 180 to the artificial muscle 100 forms an electrical potential across adjacent positive electrodes 124 and negative electrodes 126 of the reciprocating electrode stack 120 and actuates the artificial muscle 100 into a contracted state 102, as shown in FIG. 1A. In addition, removing voltage from the artificial muscle 100 removes the electrical potential and places the artificial muscle is a relaxed state 104, as shown in FIG. 1B.

Figure 1B:
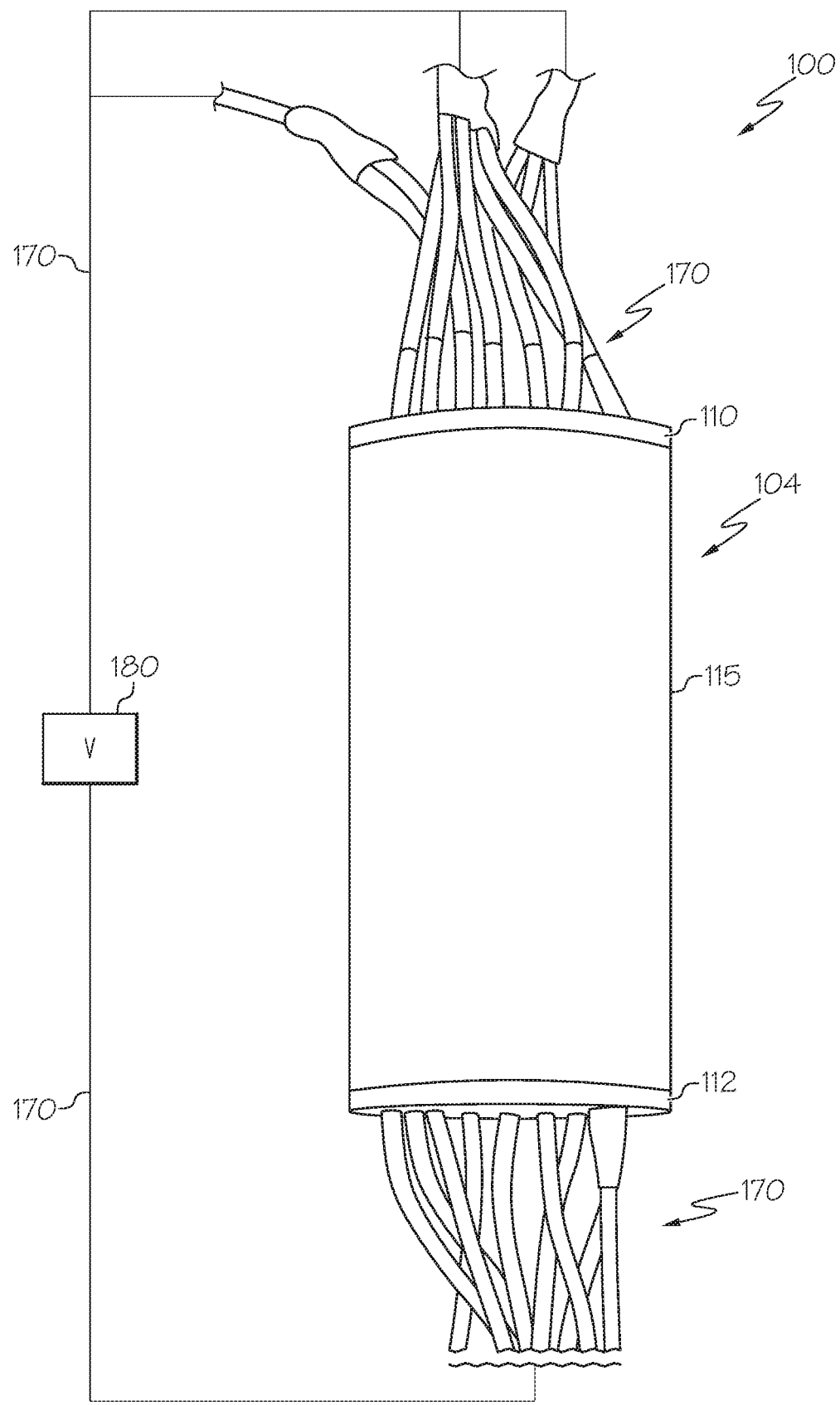
FIG. 1B depicts a side view of the artificial muscle of FIG. 1A in a relaxed state, according to one or more embodiments shown and described herein.
Figure 2A:
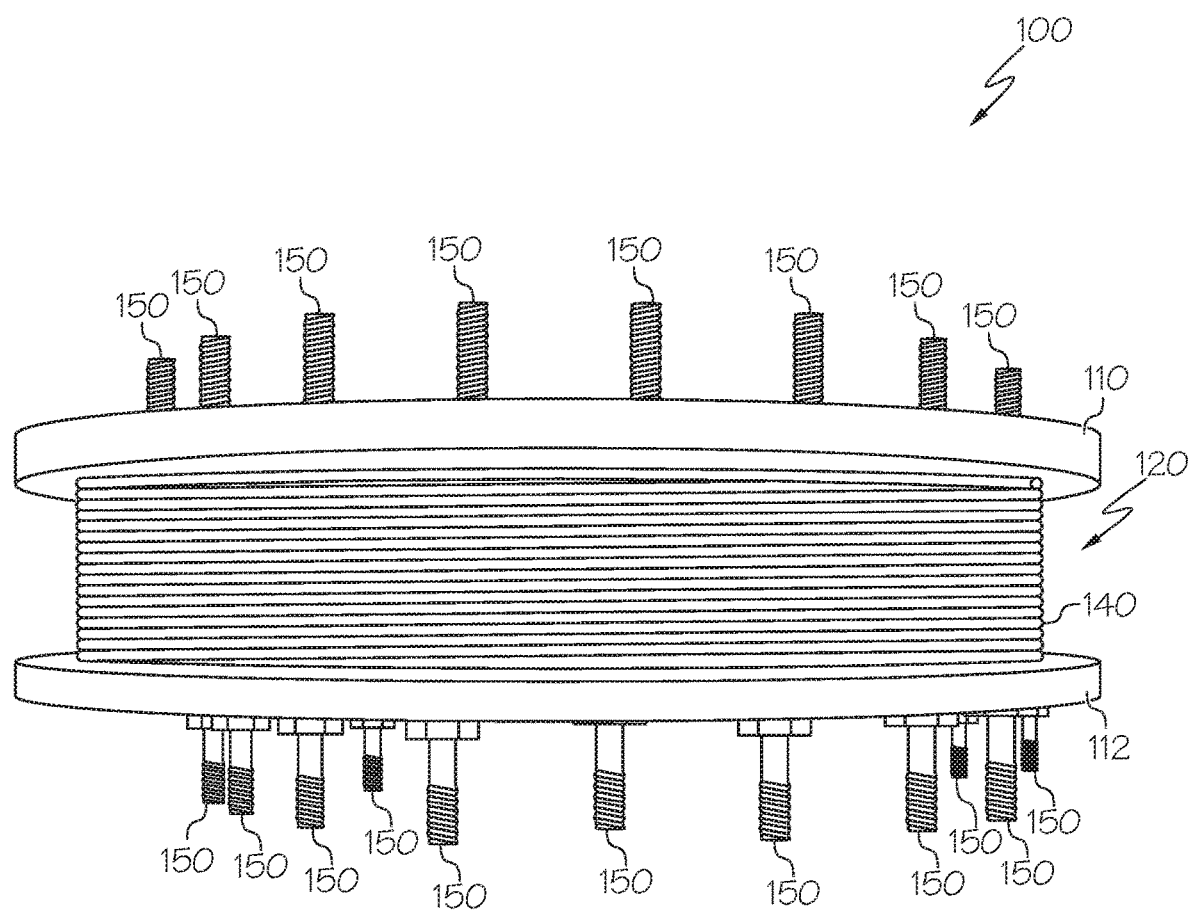
FIG. 2A depicts a side view of the artificial muscle of FIG. 1A with the flexible enclosure removed, according to one or more embodiments shown and described herein.
Figure 2B:
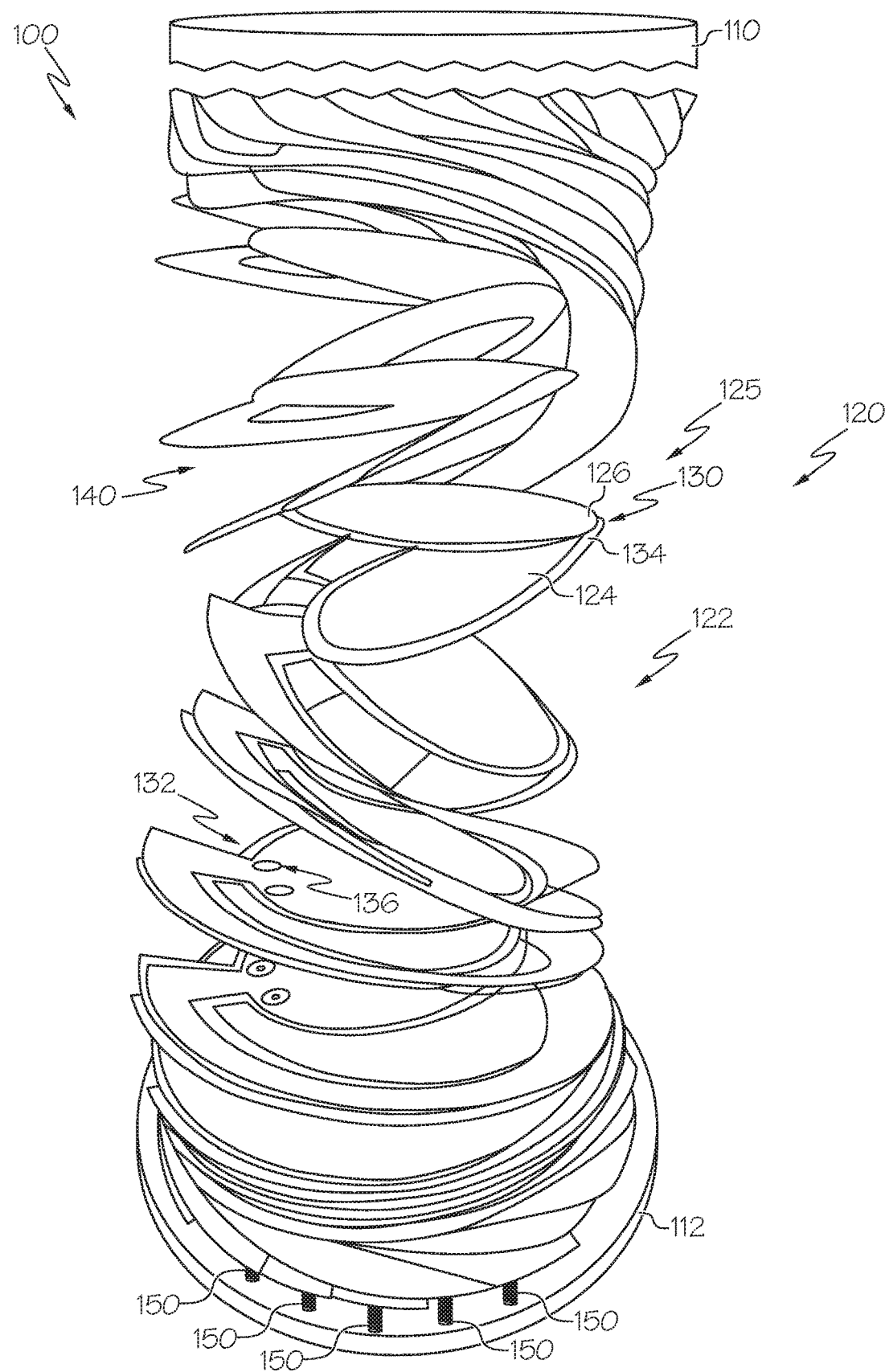
FIG. 2B depicts a side view of the artificial muscle of FIG. 1B with the flexible enclosure removed, according to one or more embodiments shown and described herein.

FIGS. 1A and 1B depict the artificial muscle 100 with the flexible enclosure 115 and FIGS. 2A and 2B depict the artificial muscle 100 without the flexible enclosure 115 to provide a view of the reciprocating electrode stack 120. The flexible enclosure 115 comprises a flexible material, such as silicone. The flexible enclosure 115 extends from the first end plate 110 to the second end plate 112, which is opposite the first end plate 110. In some embodiments, the first end plate 110 and the second end plate 112 may comprise acrylic, however, it should be understood that other rigid materials may be used. In some embodiments, both the first end plate 110 and the second end plate 112 comprise cylindrical plates, as shown in FIGS. 1A-2B. Similarly, the flexible enclosure 115 may comprise a cylindrical enclosure. However, it is contemplated that the first end plate 110 and the second end plate 112 comprise any shape, which may be chosen based on the desired end use of the artificial muscle 100 and the flexible enclosure 115 may comprise any corresponding shape to couple to and extend between the first end plate 110 and the second end plate 112 while housing the reciprocating electrode stack 120. In some embodiments, the flexible enclosure 115 is coupled to the first end plate 110 and the second end plate 112 while also enveloping the first end plate 110 and the second end plate 112. In other embodiments, the flexible enclosure 115 is coupled to the first end plate 110 and the second end plate 112, but does not completely envelop the first end plate 110 and the second end plate 112.

In addition to the reciprocating electrode stack 120, the flexible enclosure 115 also houses a dielectric fluid. A "dielectric fluid" as used herein is a medium or material that transmits electrical force with minimal to no conduction and as such has low electrical conductivity. Some non-limiting example dielectric fluids include perfluoroalkanes, transformer oils, and deionized water. The dielectric fluid minimizes unwanted electrical discharges (i.e., shorts) between electrodes 122. In addition, the dielectric fluid is disposed between the unconnected portions of adjacent electrodes 122 when the artificial muscle 100 is in a relaxed state 104. When voltage is applied to the reciprocating electrode stack 120, contracting the reciprocating electrode stack 120 into the contracted state 102, the flexible enclosure 115 may stretch radially outward to hold the dielectric fluid pushed outward from the reciprocating electrode stack 120.

Figure 3:
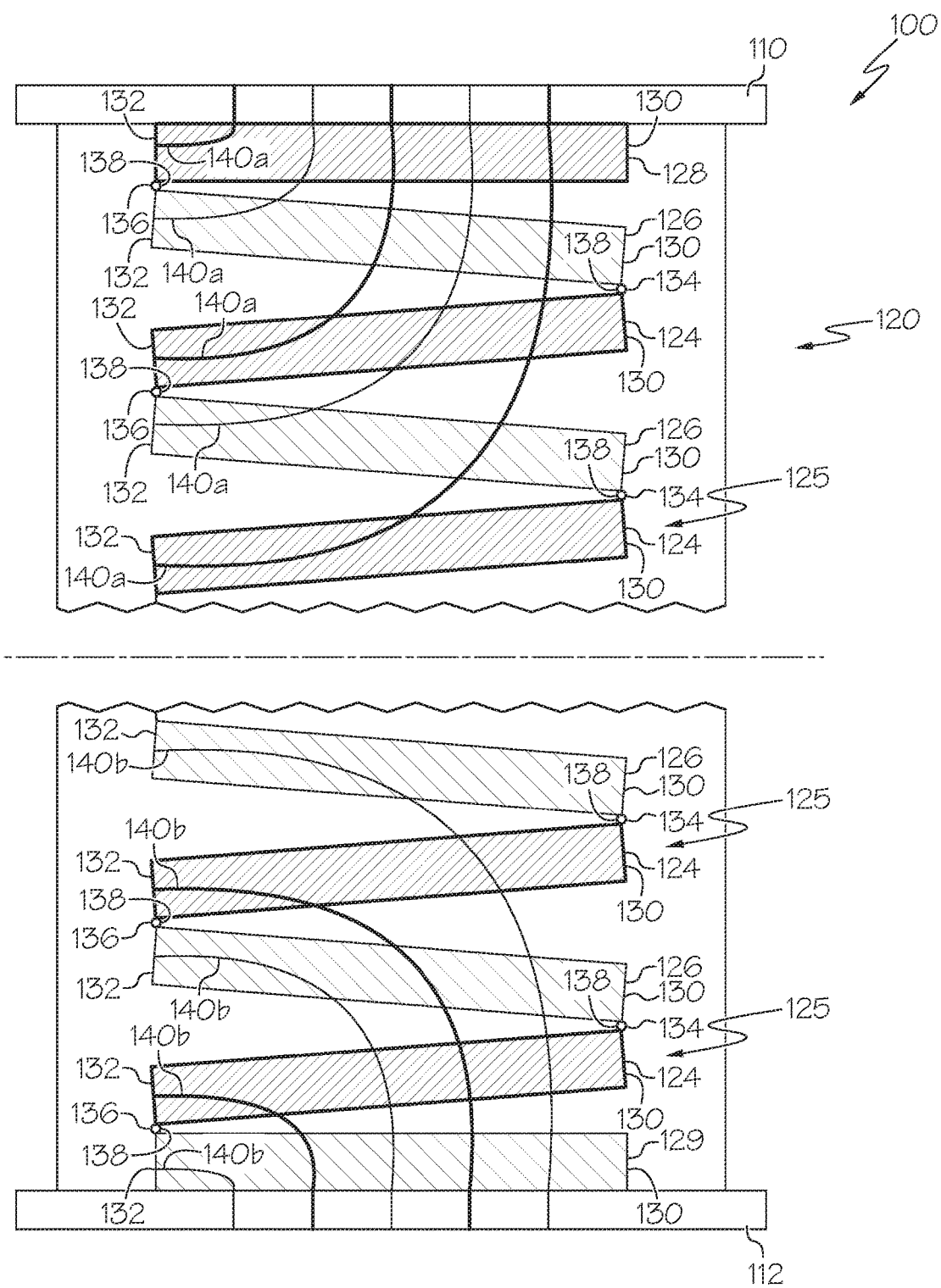
FIG. 3 schematically depicts a cross section of the artificial muscle of FIGS. 1A and 1B, according to one or more embodiments shown and described herein.

Referring now to FIG. 3, a schematic cross section of the artificial muscle 100 is depicted. As shown in FIG. 3, the reciprocating electrode stack 120 comprises a plurality of electrodes 122 arranged in one or more electrode pairs 125, each electrode pair 125 comprising a positive electrode 124 and a negative electrode 126. In some embodiments, the electrodes 122 are cylindrical electrodes, for example, in embodiments in which the first end plate 110 and the second end plate 112 are cylindrical plates and the flexible enclosure 115 is a cylindrical enclosure. However, it should be understood that embodiments of the reciprocating electrode stack 120 may include electrodes having a variety of shapes, such as rectilinear shapes. Moreover, while the reciprocating electrode stack 120 is shown with a plurality of electrode pairs 125, it should be understood that other embodiments are contemplated with a single electrode pair 125.

Each electrode pair 125 comprises a positive electrode 124 and a negative electrode 126 physically coupled to one another along a first edge portion 130 of both the positive electrode 124 and the negative electrode 126. The physical connection between the positive electrode 124 and the negative electrode 126 of a single electrode pair 125 is referred to herein as an intra-pair connection 134. Each intra-pair connection 134 is facilitated by a connective component 138. In addition, the intra-pair connection 134 is a low profile connection. For example, in some embodiments, the connective component 138 separates the first edge portion 130 of each of the positive electrode 124 and the negative electrode by no greater than the thickness of a single electrode 122. As a non-limiting example, the thickness of a single electrode 122 may be in a range of from about 0.1 millimeters (mm) to 1 mm, such as 0.2 mm, 0.3 mm, 0.4 mm, 0.5 mm, 0.6 mm, 0.7 mm, 0.8 mm, 0.9 mm, or the like. In some embodiments, the connective component 138 is a thread, such as a nylon thread. In some embodiments, the connective component 138 is an adhesive.

Referring still to FIG. 3, in embodiments comprising a plurality of electrode pairs 125, adjacent electrode pairs 125 are physically connected to each other along a second edge portion 132 of one of the two electrodes 122 of each electrode pair 125. The physical connection between electrodes 122 of an adjacent electrode pair 125 is referred to herein as an inter-pair connection 136. The connected electrodes of adjacent electrode pairs 125 include a positive electrode 124 of one electrode pair 125 and a negative electrode 126 of the other electrode pair 125. Similar to the intra-pair connections 134, the inter-pair connections 136 are facilitated by connective components 138 and are thus similarly low profile. The first edge portion 130 and the second edge portion 132 of each electrode 122 are substantially opposite one another.

When the electrodes 122 comprise cylindrical electrodes, the first edge portion 130 is diametric the second edge portion 132. As used herein, "diametric" refers to two points along the perimeter of an individual electrode 122 that are each within 10° of an antipodal position of the other. Alternatively, when the electrodes 122 comprise a rectilinear shape, the first edge portion 130 comprises a side of this rectilinear electrode that is opposite the second edge portion 132. Because the second edge portion 132 of each electrode 122 is diametric the first edge portion 130, the inter-pair connections 136 between adjacent electrode pairs 125 are diametric the intra-pair connections 134 of each electrode pair 125. This forms reciprocating physical connectivity between adjacent electrodes 122 of the reciprocating electrode stack 120, forming a zig-zag or accordion-like stack. While not intending to be limited by theory, the reciprocating physical connectivity of the reciprocating electrode stack 120 increases the power to weight ratio of the artificial muscle 100, by increasing electrode density.

Referring still to FIG. 3, the reciprocating electrode stack 120 may also comprises a first end electrode 128 positioned between and coupled to the first end plate 110 and one of the electrode pairs 125 and a second end electrode 129 positioned between and coupled to the second end plate 112 and one of the electrode pairs 125. In embodiments comprising a plurality of electrode pairs 125, the first end electrode 128 is coupled to a first electrode pair and the second end electrode is coupled to a second electrode pair. In embodiments comprising a single electrode pair, each of the first end electrode 128 and the second end electrode 129 are coupled to different electrodes 122 of the single electrode pair 125. The first end electrode 128 and the second end electrode 129 are oppositely charged. In other words, when the first end electrode 128 is a positive electrode, the second end electrode 129 is a negative electrode and when the first end electrode 128 is a negative electrode, the second end electrode 129 is a positive electrode. As shown in FIG. 3, the first end electrode 128 may be connected flat against the first end plate 110 and the second end electrode 129 may be connected flat against the second end plate 112.

Moreover, the positive and negative electrodes 124, 126 of the reciprocating electrode stack 120 are arranged in an alternating pattern such that each individual positive electrode 124 of the one or more electrode pairs 125 is positioned between and directly adjacent two negative electrodes 126 and each individual negative electrode 126 is positioned between and directly adjacent two positive electrodes 124. In other words, adjacent electrode pairs 125 are coupled together such that the positive electrode 124 of each electrode pair 125 are physically coupled to a negative electrode 126 of an adjacent electrode pair 125. In addition, when the first end electrode 128 is a positive electrode 124, it is physically coupled to a negative electrode 126 of the adjacent electrode pair 125 and when the first end electrode 128 is a negative electrode 126 it is physically coupled to a positive electrode 124 of the adjacent electrode pair 125. Similarly, when the second end electrode 129 is a positive electrode 124, it is physically coupled to a negative electrode 126 of the adjacent electrode pair 125 and when the second end electrode 129 is a negative electrode 126 it is physically coupled to a positive electrode 124 of the adjacent electrode pair 125.

It should be understood that the reciprocating electrode stack 120 has a minimum of two electrodes in any embodiment and a minimum of four electrodes in embodiments that include the first end electrode 128 and the second end electrode 129. Furthermore, it should be understood that the reciprocating electrode stack 120 may have substantially larger number of total electrodes, for example, 10 or more electrodes, 20 or more electrodes, 40 or more electrodes, 75 or more electrodes, 100 or more electrodes, or the like. Indeed, increasing the total number of electrodes increases the total actuation power of the artificial muscle 100 and the reciprocating design of the reciprocating electrode stack 120 increases the electrode density of the artificial muscle 100, facilitating the formation of relatively small artificial muscles with relatively high power. In one example, an artificial muscle 100 with a reciprocating electrode stack 120 includes 40 total electrodes and has a length measured from the first end plate 110 to the second end plate 112 (and including the first end plate 110 and the second end plate 112) of 12 mm.

Referring now to FIGS. 2A-3, the artificial muscle 100 further comprises a plurality of electrode leads 140 electrically coupled to the reciprocating electrode stack 120. The plurality of electrode leads 140 provide an electrical pathway for voltage generated by a voltage source 180 to reach each electrode 122 of the reciprocating electrode stack 120. In particular, each individual electrode lead 140 of the plurality of electrode leads 140 is electrically coupled to an individual electrode 122. In operation, electrode leads 140 electrically coupled to negative electrodes 126 of the reciprocating electrode stack 120 supply a negative voltage and the electrode leads 140 electrically coupled to positive electrodes 124 of the reciprocating electrode stack 120 supply a positive voltage.

Each individual electrode lead 140 extends from an individual electrode 122 to the first end plate 110 or the second end plate 112. In particular, the plurality of electrode leads 140 comprise a first set of electrode leads 140a that extend from an individual electrode 122 to the first end plate 110 and a second set of electrode leads 140b that extend from an individual electrode 122 to the second end plate 112. The first set of electrode leads 140a are coupled to individual electrodes 122 that are nearer the first end plate 110 than the second end plate 112 and the second set of electrode leads 140b are coupled to individual electrodes 122 that are nearer the second end plate 112 than the first end plate 110. While it is contemplated that the plurality of electrode leads 140 may comprise any suitable electrode pathway, in some embodiments, the plurality of electrode leads 140 comprises spiral electrode leads that curl around the reciprocating electrode stack 120.

Figure 4A:
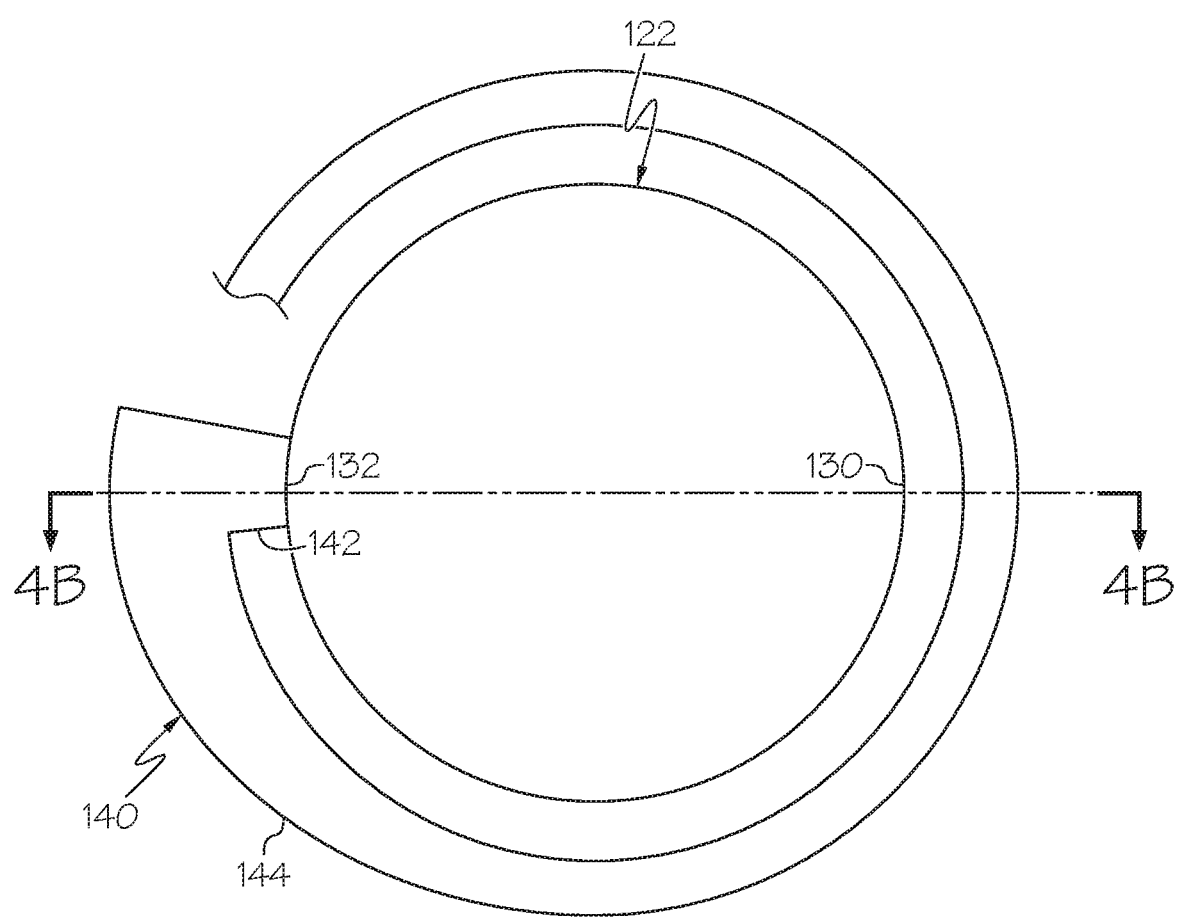
FIG. 4A schematically depicts a top view of an example electrode and an example electrode lead, according to one or more embodiments shown and described herein.
Figure 4B:
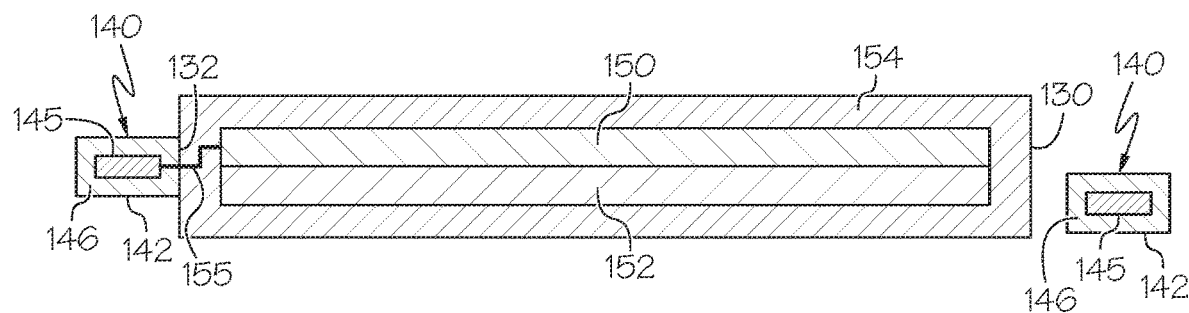
FIG. 4B is a cross sectional view of the electrode and electrode lead of FIG. 4A taken along line 4B-4B, according to one or more embodiments shown and described herein.

Referring now to FIGS. 4A and 4B, an example electrode 122 electrically and physically coupled an example electrode lead 140 is schematically depicted. The example electrode 122 is cylindrical electrode and the example electrode lead 140 is a spiral electrode lead. FIG. 4A shows a top view of the electrode 122 and electrode lead 140 and FIG. 4B is a cross section taken along line 4B-4B of FIG. 4A. As depicted in FIG. 4A, the electrode lead 140 is physically and electrically coupled to the second edge portion 132 of the electrode 122. In particular, the electrode lead 140 includes a spur segment 142 extending radially outward from the second edge portion 132 of the electrode 122 and a spiral segment 144 extending from the spur segment 142 around the electrode 122.

While only a portion of the spiral segment 144 is depicted, it should be understood that, as depicted in FIG. 2B, the spiral segment 144 curls around the reciprocating electrode stack 120 and extends from the spur segment 142 to one of the first end plate 110 or the second end plate 112. The spiral segment 144 may curl around the reciprocating electrode stack 120 by less than a single circumference of the plurality of electrodes 122, a single circumference of the plurality of electrode 122, or greater than a single circumference of the plurality of electrodes 122, even multiple times around the circumference of the plurality of electrodes 122. Indeed, electrode leads 140 coupled to electrodes 122 that are nearer the center of the reciprocating electrode stack 120 (as indicated by a central plane 15 in FIG. 3) curl around the reciprocating electrode stack 120 a greater number of times than electrode leads 140 that are coupled to electrodes 122 nearer the first end plate 110 or the second end plate 112.

Referring now to FIG. 4B, in some embodiments, the electrode 122 comprises a flexible metal film 152 surrounded by polymer cover coating 154. In some embodiments, the electrode 122 also comprises an inner polymer film 150 coupled to the flexible metal film 152 to function as backing for the flexible metal film 152. In some embodiments, the inner polymer film 150 comprises polyester and the flexible metal film 152 comprises aluminum or copper. However, it should be understood that any suitable polymers and metals for forming an electrode are contemplated. In addition, it should be understood that additional interlayers may be positioned between the inner polymer film 150 and the flexible metal film 152. The polymer cover coating 154, which is wrapped around the inner polymer film 150 and the flexible metal film 152, comprises a different polymer than the inner polymer film 150. For example, in some embodiments, the polymer cover coating 154 comprises a polyimide.

Referring still to FIG. 4B, in some embodiments, the electrode lead 140 comprises a flexible metal lead 145 surrounded by a polymer lead coating 146. Similar to the flexible metal film 152 of the electrode 122, the flexible metal lead 145 comprises a flexible, conductive metal material such as aluminum or copper. Further, the polymer lead coating 146 may comprise any suitable polymer material, such as polyester, polyimide, or the like. The flexible metal lead 145 is electrically coupled to the flexible metal film 152 such that voltage generated by the voltage source 180 is applied to the flexible metal film 152 via the flexible metal lead 145. In some embodiments, the flexible metal lead 145 is directly connected to the flexible metal film 152 and in other embodiments an interconnect 155 extends therebetween.

Referring now to FIGS. 1A-3, in some embodiments, the first end plate 110 and the second end plate 112 include electrical connectors 160 to electrically connect the plurality of electrode leads 140 to external transmission lines 170 that extend from the electrical connectors 160 to the voltage source 180. Electrical connectors 160 may be arranged on the first end plate 110 in a radial array and also arranged on the second end plate 112 in a radial array. Thus, the first set of electrode leads 140a are coupled to the first end plate 110 in a radial array and the second set of electrode leads 140b are coupled to the second end plate 112 in a radial array. The radial array of the electrical connectors 160 of both the first end plate 110 and the second end plate 112 are positioned radially outward from the reciprocating electrode stack 120 encircling the reciprocating electrode stack 120. Thus, the reciprocating electrode stack 120 does not impede connections between the electrode leads 140 and the electrical connectors 160. Further, the radial array of electrical connectors 160 provide a different location for each spiral segment 144 of the plurality of electrode leads 140 to reach the first end plate 110 or the second end plate 112. Thus, each of the first electrode leads 140a can follow the same spiraling pathway around the reciprocating electrode stack 120 and connect to an individual electrical connector 160 at the first end plate 110 and each of the second electrode leads 140b can follow the same spiraling pathway around the reciprocating electrode stack and connect to an individual electrical connector 160 at the second end plate 112.

Moreover, while FIGS. 1-3A depict embodiments in which the plurality of electrode leads 140 are electrically coupled to the electrical connectors 160 of the first end plate 110 and the second end plate 112, in other embodiments, the electrode leads 140 may extend from the reciprocating electrode stack 120 directly to the voltage source 180. For example, the electrode leads 140 may extend from individual electrodes 122, through the first end plate 110 or the second end plate 112, and outward to the voltage source 180.

In operation, the artificial muscle 100 may be contracted by applying a voltage generated by the voltage source 180 to the reciprocating electrode stack 120. In particular, voltage may be generated by the voltage source 180 and applied to the plurality of electrodes 122 of the reciprocating electrode stack 120, thereby inducing contraction of each electrode pair 125 of the one or more electrode pairs 125 such that the first end plate 110 and the second end plate 112 and drawn toward one another, contracting the artificial muscle 100 into the contracted state 102. While not intending to be limited by theory, applying negative voltage to the negative electrodes 126 of the reciprocating electrode stack 120 and applying positive voltage to the positive electrodes 124 of the reciprocating electrode stack 120 forms an electrical potential across the alternating positive electrodes 124 and negative electrodes 126, contracting the artificial muscle 100. Indeed, the positive and negative electrodes 124, 126 of each electrode pair 125 are drawn together, neighboring positive and negative electrodes 124, 126 of adjacent electrode pairs 125 are drawn together, and the first and second end electrodes 128, 129 are drawn toward their respective neighboring electrodes 122.

Once the artificial muscle 100 is contracted into the contracted state 102, continued application of voltage holds the artificial muscle 100 in the contracted state 102. Further, removing voltage from the reciprocating electrode stack 120 releases each electrode pair 125, such that the artificial muscle relaxes from the contracted state 102 to the relaxed state 104. This allows adjacent electrodes 122 to move apart freely and allows dielectric fluid to fill the spaces between adjacent electrodes 122. As a non-limiting example operation, the artificial muscle 100 may provide actuating force to a robotic arm analogous to the actuating force of a bicep muscle. However, it should be understood that the artificial muscle 100 may be implemented in a variety of other robotic and mechanical applications that utilize a contracting actuation mechanism.

It should now be understood that embodiments described herein are directed to artificial muscles that include a reciprocating electrode stack having electrode pairs that each include a positive and a negative electrode physically coupled to one another along one edge, where electrodes of adjacent pairs are physically connected along an opposite edge such that the electrodes are connected in an alternating, zigzag pattern. The arrangement of the reciprocating electrode stack increases the electrode density to form an artificial muscle with a high actuation power per unit volume.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle comprising:
a first end plate opposite a second end plate;
a flexible enclosure extending from the first end plate to the second end plate and housing a dielectric fluid;
a reciprocating electrode stack housed within the flexible enclosure and coupled to and extending between the first end plate and the second end plate, wherein:
the reciprocating electrode stack comprising one or more electrode pairs, each electrode pair comprising a positive electrode and a negative electrode physically coupled to one another along a first edge portion of the positive electrode and the negative electrode; and
a plurality of electrode leads electrically coupled to the reciprocating electrode stack, wherein each individual electrode lead of the plurality of electrode leads extends from an individual electrode of the reciprocating electrode stack to the first end plate or the second end plate.

2. The artificial muscle of claim 1, wherein each individual electrode of the reciprocating electrode stack comprises a cylindrical electrode.

3. The artificial muscle of claim 1, wherein the reciprocating electrode stack comprises a plurality of electrode pairs.

4. The artificial muscle of claim 3, wherein:
adjacent electrode pairs are physically connected to each other along a second edge portion of one of the two electrodes of each adjacent electrode pair; and
the second edge portion of each electrode is diametric the first edge portion.

5. The artificial muscle of claim 3, wherein:
each individual positive electrode of the plurality of electrode pairs is positioned between and directly adjacent two negative electrodes; and
each individual negative electrode is positioned between and directly adjacent two positive electrodes.

6. The artificial muscle of claim 1, wherein the reciprocating electrode stack further comprises a first end electrode coupled to the first end plate and a first electrode pair of the one or more electrode pairs and a second end electrode coupled to the second end plate and a second electrode pair of the one or more electrode pairs.

7. The artificial muscle of claim 1, wherein the plurality of electrode leads comprise spiral electrode leads that curl around the reciprocating electrode stack.

8. The artificial muscle of claim 7, wherein:
the spiral electrode leads each comprise a spur segment coupled to and extending radially outward from a second edge portion of an individual electrode and a spiral segment curling around the reciprocating electrode stack; and
the second edge portion of each electrode is diametric the first edge portion.

9. The artificial muscle of claim 1, wherein:
the plurality of electrode leads comprise a first set of electrode leads each extending from an individual electrode to the first end plate and a second set of electrode leads each extending from an individual electrode to the second end plate; and
the first set of electrode leads are coupled to the first end plate in a radial array and the second set of electrode leads are coupled to the second end plate in a radial array.

10. The artificial muscle of claim 1, wherein the first end plate and the second end plate each comprise electrical connectors arranged in a radial array and electrically coupled to an individual electrode lead of the plurality of electrode leads.

11. The artificial muscle of claim 10, wherein a plurality of external transmission lines electrically couple the electrical connectors to a voltage source.

12. The artificial muscle of claim 10, wherein the radial array of the electrical connectors of both the first end plate and the second end plate are positioned radially outward from the reciprocating electrode stack.

13. A method of contracting an artificial muscle, the method comprising:
generating voltage using a voltage source electrically coupled to a plurality of electrode leads of an artificial muscle, the artificial muscle further comprising:
a first end plate opposite a second end plate;
a flexible enclosure extending from the first end plate to the second end plate and housing a dielectric fluid; and
a reciprocating electrode stack housed within the flexible enclosure and coupled to and extending between the first end plate and the second end plate, wherein:
the reciprocating electrode stack comprises a plurality of electrodes arranged in one or more electrode pairs, each electrode pair comprising a positive electrode and a negative electrode physically coupled to one another along a first edge portion of the positive electrode and the negative electrode and each individual electrode electrically coupled to an individual electrode lead of the plurality of electrode leads; and
applying voltage generated by the voltage source to the reciprocating electrode stack, thereby inducing contraction of each electrode pair such that the first end plate and the second end plate and drawn toward one another, contracting the artificial muscle into a contracted state.

14. The method of claim 13, further comprising removing voltage from the reciprocating electrode stack, thereby releasing each electrode pair such that the artificial muscle relaxes from the contracted state into a relaxed state.

15. The method of claim 13, wherein the voltage applied to the reciprocating electrode stack comprises less than 10 kilovolts.

16. The method of claim 13, wherein:
the reciprocating electrode stack comprises a plurality of electrode pairs;
adjacent electrode pairs are physically connected to each other along a second edge portion of one of the two electrodes of each electrode pair; and
the second edge portion of each electrode is diametric the first edge portion.

17. The method of claim 13, wherein the plurality of electrode leads comprise spiral electrode leads that curl around the reciprocating electrode stack.

18. An artificial muscle comprising:
a first end plate opposite a second end plate;
a flexible enclosure extending from the first end plate to the second end plate and housing a dielectric fluid;
a reciprocating electrode stack housed within the flexible enclosure and coupled to and extending between the first end plate and the second end plate, wherein:
the reciprocating electrode stack comprises a plurality of cylindrical electrode pairs;
each cylindrical electrode pair comprises a positive electrode and a negative electrode physically coupled to one another along a first edge portion of the positive electrode and the negative electrode;
adjacent cylindrical electrode pairs are physically connected to each other along a second edge portion of one of the two cylindrical electrodes of each adjacent cylindrical electrode pair; and
the second edge portion of each cylindrical electrode is diametric the first edge portion; and
a plurality of spiral electrode leads electrically coupled to the reciprocating electrode stack, wherein each individual spiral electrode lead of the plurality of spiral electrode leads extends from an individual cylindrical electrode of the reciprocating electrode stack to the first end plate or the second end plate and curls around the reciprocating electrode stack.

19. The artificial muscle of claim 18, wherein the spiral electrode leads each comprise a spur segment coupled to and extending radially outward from the second edge portion of an individual cylindrical electrode and a spiral segment curling around the reciprocating electrode stack.

20. The artificial muscle of claim 18, wherein:
the first end plate and the second end plate each comprise electrical connectors arranged in a radial array and electrically coupled to an individual spiral electrode lead of the plurality of spiral electrode leads;
the radial array of the electrical connectors of both the first end plate and the second end plate are positioned radially outward from the reciprocating electrode stack; and
a plurality of external transmission lines electrically couple the electrical connectors to a voltage source.

\* \* \* \* \*